United States Patent
Blumhofer et al.

(10) Patent No.: US 9,639,938 B2
(45) Date of Patent: May 2, 2017

(54) MATCHING PATIENT IMAGES OF DIFFERENT IMAGING MODALITY USING ATLAS INFORMATION

(71) Applicant: Brainlab AG, Feldkirchen (DE)

(72) Inventors: Andreas Blumhofer, Neubiberg (DE); Bálint Varkuti, München (DE); Jens Schmaler, Regensburg (DE)

(73) Assignee: BRAINLAB AG, Munich (DE)

( * ) Notice: Subject to any disclaimer, the term of this patent is extended or adjusted under 35 U.S.C. 154(b) by 57 days.

(21) Appl. No.: 14/437,784

(22) PCT Filed: Jun. 28, 2013

(86) PCT No.: PCT/EP2013/063640
§ 371 (c)(1),
(2) Date: Apr. 22, 2015

(87) PCT Pub. No.: WO2014/063840
PCT Pub. Date: May 1, 2014

(65) Prior Publication Data
US 2015/0294467 A1    Oct. 15, 2015

Related U.S. Application Data

(63) Continuation-in-part of application No. PCT/EP2012/071241, filed on Oct. 26, 2012.

(51) Int. Cl.
*G06K 9/00*    (2006.01)
*G06T 7/00*    (2017.01)
(Continued)

(52) U.S. Cl.
CPC .......... *G06T 7/0026* (2013.01); *G06T 3/0056* (2013.01); *G06T 7/0012* (2013.01);
(Continued)

(58) Field of Classification Search
None
See application file for complete search history.

(56) References Cited

U.S. PATENT DOCUMENTS

| | | | |
|---|---|---|---|
| 6,754,374 B1* | 6/2004 | Miller | G06K 9/32 382/128 |
| 2005/0182319 A1* | 8/2005 | Glossop | A61B 34/20 600/424 |

(Continued)

FOREIGN PATENT DOCUMENTS

| | | |
|---|---|---|
| EP | 1239921 | 9/2002 |
| EP | 1814453 | 8/2007 |

(Continued)

OTHER PUBLICATIONS

European Patent Office, International Search Report of PCT/EP2013/063640, Oct. 18, 2013, pp. 1-3, European Patent Office, Rijswijk, The Netherlands.

*Primary Examiner* — Sean Conner
(74) *Attorney, Agent, or Firm* — Middleton Reutlinger

(57) ABSTRACT

The present invention relates to a medical data processing method of transforming a representation of an anatomical structure of a patient in a first imaging modality into a representation of the anatomical structure in a second, other imaging modality, the method being constituted to be executed by a computer and comprising the following steps: acquiring first modality image data describing the first modality medical image containing the representation of the anatomical structure in the first imaging modality; acquiring atlas data describing a first modality atlas image describing a general structure of the anatomical structure in the first imaging modality, the atlas data containing information about the representation of the general structure in the second imaging modality; determining, based on the first modality image data and the atlas data, a first matching (Continued)

transformation between the first modality medical image and the first modality atlas image; determining, based on the first matching transformation and the first modality atlas image and the information about the representation of the general structure in the second imaging modality second modality, a second modality image representation of the first modality medical image.

16 Claims, 2 Drawing Sheets

(51) Int. Cl.
    *G06T 3/00*     (2006.01)
    *G06T 11/00*    (2006.01)
(52) U.S. Cl.
    CPC .......... *G06T 7/0024* (2013.01); *G06T 7/0038* (2013.01); *G06T 7/0081* (2013.01); *G06T 7/0097* (2013.01); *G06T 11/008* (2013.01); *G06T 2207/10004* (2013.01); *G06T 2207/10076* (2013.01); *G06T 2207/10081* (2013.01); *G06T 2207/10084* (2013.01); *G06T 2207/10116* (2013.01); *G06T 2207/20081* (2013.01); *G06T 2207/20104* (2013.01); *G06T 2207/20128* (2013.01); *G06T 2207/20221* (2013.01); *G06T 2207/30004* (2013.01); *G06T 2207/30196* (2013.01)

(56) References Cited

U.S. PATENT DOCUMENTS

| | | |
|---|---|---|
| 2006/0004274 A1 | 1/2006 | Hawman |
| 2007/0038058 A1* | 2/2007 | West .................. A61N 5/1049 600/407 |
| 2008/0188741 A1 | 8/2008 | Mallya et al. |
| 2011/0069873 A1 | 3/2011 | Azemoto et al. |
| 2011/0085716 A1* | 4/2011 | Chefd'hotel ......... G06K 9/6215 382/128 |
| 2012/0314924 A1 | 12/2012 | Carlton et al. |

FOREIGN PATENT DOCUMENTS

| | | |
|---|---|---|
| EP | 1868157 | 12/2007 |
| EP | 1890261 | 2/2008 |
| EP | 2131212 | 12/2009 |

\* cited by examiner

MATCHING PATIENT IMAGES OF DIFFERENT IMAGING MODALITY USING ATLAS INFORMATION

The present invention is directed to a method, in particular data processing method, of determining a matching transformation for matching medical images describing an anatomical structure of a patient, wherein images of different imaging modality are matched.

The invention is further directed to a corresponding program, in particular computer program, a computer running a program and a signal wave carrying information which represents the program.

In many applications, it is desirable to compare the position which the representation of a specific anatomical structure has in different medical images in order to for example determine a change in the position of the anatomical structure. For example, some medical procedures carried out on the brain require determining a difference between the position which an anatomical structure in the brain has before and after performing craniotomy. For example, a magnetic resonance image is taken before craniotomy which allows for determining the first position of the brain in the skull. After performing craniotomy, a computer tomography image of the brain is acquired which allows for determining the second position of the brain in the skull. It would now be desirable to allow for a comparison between the two images.

However, different imaging modalities, in the above case magnetic resonance tomography and computer tomography (also called computed tomography), in general lead to different image colour contrast scales (which are associated with the respective imaging modality. For example the grey values used to describe the anatomical structure in the magnetic resonance image differ from the grey values used to describe the anatomical structure in the computer tomography image. Preferably, comparison of the images is achieved by fusing the two images, which may be hampered, though, for example by data processing instabilities due to the difference in the respectively used grey values.

A problem to be solved by the invention therefore is to provide a stable and reliable way of comparing medical images which were generated based on applying different imaging modalities.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

EXEMPLARY SHORT DESCRIPTION OF THE INVENTION

In this chapter, a short description of an example of the invention is offered which shall not be construed as limiting the invention to this example.

The invention is direct to a medical data processing method of transforming a representation of an anatomical structure of a patient in a medical image of a first imaging modality (first modality medical image) into a representation of the anatomical structure in a second, other imaging modality (second modality image representation). The anatomical structure can be any anatomical structure which is known to be part of a patient's body, preferably it is the brain. Based on the first modality medical image describing the representation of the anatomical structure in the first imaging modality and based on a first modality atlas image describing a general structure of the anatomical structure in the first imaging modality, a first matching transformation between the first modality medical image and the first modality atlas image is determined. The first modality atlas image is described by atlas data which also contains information about the representation of the general structure in the second imaging modality. This information may be embodied by or determined from a second modality atlas image contained in the atlas data. The first imaging modality preferably is MR, the second imaging modality preferably is CT. Based on the first matching transformation and the first modality atlas image and the information about the representation of the general structure in the second imaging modality second modality, a second modality image representation of the first modality medical image is determined. Preferably, also a second modality medical image is acquired. Then, a second matching transformation between the second modality image representation and the second modality medical image can be determined. Thereby, the appearance of the anatomical structure in the transformed first modality medical image (i.e. in the second modality image representation) can be compared with its appearance in the second modality medical image. The transformations determined or applied, respectively, preferably are elastic fusion transformations. Preferably, the transformations are determined taking into account representation properties such as element representation information and representation classes of individual image elements in the (image) representations between which the transformations are determined. The representation classes can describe tissue classes. The invention preferably also comprises features which are directed to avoiding computational faults if there are major differences between the representation of the anatomical structure in the second modality image representation and the second modality medical image.

GENERAL DESCRIPTION OF THE INVENTION

In order to solve the afore-mentioned problem, the present invention provides in particular a method (which is in particular a data processing method such as a medical data processing method) of transforming a representation of an anatomical structure of a patient in a first imaging modality to a representation of the anatomical structure in a second, other imaging modality. The anatomical structure may be any anatomical structure contained in the patient's body, for example the anatomical structure comprises (in particular consists of) at least one of bony tissue (for example a part of a bone—such as for example of the skull—or cartilage) and soft tissue (for example a part of the lung or the brain). In a particular embodiment, the anatomical structure comprises at least part of the brain. However, the anatomical structure may also comprise at least part of the heart or an intestinal organ such as the stomach or the colon. Alternatively or additionally, the anatomical structure may comprise a bony structure such as at least part of the skull.

The first modality medical image is generated (in particular has been generated before executing the disclosed method) based on first modality image data which has been generated based on applying the first imaging modality to the anatomical structure, and the second modality medical image is generated (in particular has been generated before executing the disclosed method) based on second modality medical image data which has been generated based on applying the second imaging modality to the anatomical structure. The second imaging modality preferably is different from the first imaging modality. In particular, the first imaging modality is magnetic resonance tomography, and the second imaging modality is computed tomography or x-ray. The type of imaging modality of the first imaging modality and the second imaging modality is preferably described by imaging modality data which is preferably also acquired during the inventive method. For example, the first modality data may comprise imaging modality data describing the first imaging modality (in particular the type of the first medical imaging modality, for example by indicating that the first imaging modality is magnetic resonance tomography) and the second modality image data may comprise imaging modality data describing the second imaging modality (in particular the type of the second medical imaging modality, for example by indicating that the second imaging modality is computer tomography or x-ray).

Within the framework of this disclosure, the term of imaging modality refers to a medical imaging technique and in particular refers to the type of energy which is applied to the anatomical structure in order to generate (medical) image data, in particular a medical image. The type of energy may for example be defined by the type of electromagnetic radiation applied to the anatomical structure. The respective type of energy is applied by an analytical device such as e.g. an x-ray tube, a computer tomograph, an ultrasound head or a magnetic resonance tomograph. An analytical device is in the framework of this disclosure also called analytical apparatus, imaging device, or imaging apparatus. Examples of imaging modalities include (but are not limited to) x-ray, computed x-ray tomography (also called computed tomography and abbreviated as CT), magnetic resonance tomography (abbreviated as MR or MRT), and ultrasound imaging. Within the framework of this disclosure, the term of imaging modality is also called medical imaging modality in order to underline the application of the imaging modality in the framework of a medical procedure. A synonymous term for medical imaging modality is medical imaging method which may also be used in this disclosure.

The disclosed method preferably comprises steps of acquiring first modality image data describing the first modality medical image, wherein the first modality image data has been generated by applying the first imaging modality (to the anatomical structure). According to preferred embodiment, the disclosed method comprises a step of acquiring second modality image data describing the second modality medical image, wherein the second modality image has been generated by applying the second imaging modality (to the anatomical structure). The first modality medical image contains the representation of the anatomical structure in the first imaging modality, the second modality medical image contains the representation of the anatomical structure in the second imaging modality. The process of generating the first modality image data and the second modality image data is not necessarily part of the disclosed method. However, steps of applying the first imaging modality and/or the second imaging modality and corresponding generation of the first modality image data and/or the second modality image data, respectively, may according to a particular embodiment also be part of the disclosed method.

The first modality medical image and the second modality medical image each contain a representation of the aforementioned anatomical structure. However, the representation of the anatomical structure may differ between the first modality medical image and the second modality medical image in particular with regard to at least one of the colour values and contrast values used to represent the anatomical structure and with regard to the spatial properties (in particular at least one of position and orientation) of the anatomical structure for example relative to image features surrounding the anatomical structure (which represent in particular other anatomical structures contained in the patient's body) or its geometric properties (in particular at least one of size—in particular volume—and shape).

Preferably, atlas data is acquired which describes a first modality atlas image. The first modality atlas image describes in particular a general structure of the anatomical structure in the first imaging modality, in particular the atlas data was generated based on medical image data which was generated by applying the first imaging modality. The atlas data in particular contains information describing the general structure of the anatomical structure (in this disclosure also referred to as general anatomical structure) in particular in a medical image (i.e. in particular by way of a medical image). The atlas data preferably contains element representation information which describes the representation of physical structures, for example the anatomical elements (referred to as "atlas elements") of the general anatomical structure in atlas images described by the atlas data. This representation corresponds to the representation of the physical structures in an image which is generated by means of an analytical device from a patient having for example an anatomical structure which is identical to the general anatomical structure. The influence of the generating process on the representation of the one or more physical structures is represented by a parameter set (for example, scanning parameters such as the type of analytical device used to generate the medical image data and/or the measurement parameters which are set, in particular adjusted, on the analytical device and have an influence on the representation). The parameter set represents and in particular comprises one or in particular more parameters (also called representation parameters, such as the type of analytical device used for generating the medical image data and for example the magnetic field strength in an MRT device or the acceleration voltage in CT devices used to generate the medical image data) which reflect and in particular are parameters which have an influence on the representation of the image elements in the medical image which serves as a basis for generating the atlas image. This at least one parameter (in particular its value and/or values) is preferably described by the element representation information and therefore the atlas data.

The atlas data is acquired in particular from an anatomical atlas which typically consists of a plurality of generic models of objects, wherein the generic models of the objects together form a complex structure. The atlas data may therefore also be called generic patient model data. The atlas image is generated based on in particular a statistical analysis of the anatomy of the bodies of a plurality of human bodies, more particularly based on a statistical analysis of the anatomy of an anatomical body structure in a plurality of human bodies corresponding to the aforementioned anatomical structure of the patient. The atlas of a femur, for example, can comprise the head, the neck, the body, the greater trochanter, the lesser trochanter, and the lower extremity as objects which may complex structure. The atlas of a brain, for example, can comprise a telencephalon, the cerebellum, the diencephalon, the pons, the mesencephalon and the medulla oblongata as the objects making up the complex structure. Examples of the aforementioned influences on the representation include influences on the image values which represent the physical structures, such as for instance influences on a grey value (representing the image value) which represents the anatomical element, or influences on the position of an image value in a colour space which represents the anatomical element. Other examples include influences on contrast, image value range, gamut, etc. The atlas data describes in particular an atlas image of the general anatomical structure in the first imaging modality (also called first modality atlas image) and comprises information about the representation of the general structure in the second imaging modality. The information about the representation of the general structure in the second imaging modality is preferably included in a look-up table contained in the atlas data, further preferably it is determined from an atlas image of the general anatomical structure in the second imaging modality (also called second modality atlas image). The second modality atlas image then is included in the atlas data. The information about the representation of the general structure is determined based on the second modality atlas image.

The general structure (and therefore also the atlas data) is preferably generated outside of the disclosed method based on medical image information which is gathered from a plurality of human bodies. Preferably, these bodies share a common characteristic such as for example at least one of gender, age and ethnicity. However, it is also possible and in the framework of the disclosed method to use atlas data describing a general structure which was generated on the basis of medical image information which was gathered from human bodies which do not share a common characteristic such as for example ethnicity, in particular the atlas data may have been generated on the basis of human bodies of different ethnicity. The general structure represents in particular the geometry (in particular at least one of size—in particular volume—and shape) of the anatomy of at least part of which was generated on the basis of the statistic analysis of the plurality of human bodies. For example, the general structure represents the most probable geometry of a patient's body having a specific characteristic such as at least one of gender, age and ethnicity. In a particular embodiment, the general structure may have been generated also on the basis of information about a specific pathologic state, for example the plurality of human bodies serving as a basis for the general structure may share a common pathologic state (such as a tumour disease or an anatomic anomaly). The representation of the general structure will vary between different imaging modalities. The representation is understood to encompass in particular the image appearance of the anatomical structure represented by the general structure in a specific image modality which is governed by for example the colour values assigned to specific physical structures (for example tissue—in particular soft tissue and bony tissue, and fluids such as liquids or gas, in particular liquids such a liquor or a gas such as air) in the respective imaging modality. The representation is described by the aforementioned element representation information. For example, the colour values generated by a computed tomography will be in a grey value scale which is defined in the Hounsfield scale and represents the absorbance of physical structures for the x-rays with which the physical structures are irradiated to generate a computed tomography. In this case, bony tissue will be rendered in lighter grey values towards the white end of the grey scale, and soft tissue and fluids will be rendered in darker grey values towards the black end of the grey scale. Alternatively or additionally, the image appearance may be governed by colour contrasts—this would be the case in particular if the applied imaging modality is magnetic resonance tomography. In magnetic resonance imaging, physical structures are delineated from one another by colour contrasts which depend in particular on the magnetic field strength, the type of magnetic pulse sequence, the considered type of magnetic relaxation (for example $T_1$ or $T_2$) and the magnetic behaviour of the physical structure in an external magnetic field. The atlas data comprises in particular information about the representation of the general structure in the first imaging modality and in the second imaging modality. This information is contained in particular in the element representation information. Furthermore, the atlas data in particular comprises information which allows to map between the representation of a specific general structure in different imaging modalities (in particular in the first imaging modality and the second imaging modality). This information in particular allows to determine how a specific part of the general structure, the appearance of which is known in the first imaging modality, would appear in the second imaging modality. To this end, the atlas data was preferably generated based on a statistical analysis of a plurality of medical images of anatomical structures corresponding to the general structure which were taken with the first imaging modality in order to generate the first modality atlas image and also based on a statistical analysis of a plurality of medical images of the respective anatomical structures which were taken with the second imaging modality in particular in order to generate the second modality atlas image. The atlas data then includes for example correspondence data describing which image features in the first modality atlas image correspond to the respective image features in the second modality atlas image in particular by assigning them to the respective anatomical structure which they represent.

The atlas data preferably comprises atlas geometry information which describes the geometric properties (in particular at least one of size—in particular volume—and shape) of the general anatomical structure. The spatial information can comprise only one set of static spatial information, i.e. spatial information which does not change over time and only provides one set of spatial properties for the general anatomical structure, or can comprise a plurality of sets of static spatial information which respectively describes the spatial properties of the general anatomical structure in different states, for instance at different points in time during for example a vital movement such as for example a breathing cycle. The vital movement is a movement of parts of the body due to vital functions of the body, such as for example breathing and/or the heart beat and/or digestive movements. The term "vital movements" covers any kind of movement of the body which is performed unconsciously and in particular controlled by the brain stem. The atlas spatial information can also describe different movement or posture states of the patient, such as the patient running, walking, standing or lying down. It can also cover different pathological states of a patient, such as a patient with an infection or a tumour in a particular part of the body, all particular states of a patient during surgery such as a patient within an exposed brain (i.e. in a state after craniotomy) resulting in a brain shift (which can in turn depend on the positioning of the head). The term "posture" as used here refers in particular to different positions of the extremities of the body, such as for example raised or lowered hands.

For example, representation class data is acquired which describes a representation class of the image elements describing the anatomical structure in the first modality medical image, the second modality medical image, the first modality atlas image and—as far as applicable—the second modality atlas image. The representation class describes in particular at least one of the aforementioned colour contrasts, colour values and the type of physical structure represented by the image elements. In a preferred embodiment, the representation class data comprises the element representation information, which then describes in particular the representation class of the respective image element(s). The physical structure can be for example an anatomical structure (such as soft tissue or bony tissue) or a fluid as mentioned above. In particular, anatomical structures are assigned tissue classes which define the type of tissue contained in the anatomical structure represented by the respective image elements. On this basis, the above-described mapping is established between image elements in the first modality atlas image and image elements in the second modality atlas image which represent the same anatomical structure. This mapping preferably is also contained in the atlas data.

Preferably, a first matching transformation is determined based on the first modality image data and the atlas data. The first matching transformation is in particular a matching transformation between the image information of the first modality image data and the first modality atlas image. Within the context of this disclosure, a matching transformation is understood to be in particular a mapping function (more particularly, a linear mapping function) for mapping information (in particular positions) defined in a reference system (in particular positional reference system) used to define for example the positions in a first data set onto information (in particular positions) defined in a (in particular different) reference system (in particular positional reference system) used to define for example the positions in a second data set. A transformation can be determined based on for example executing at least one of an image segmentation algorithm and an image fusion algorithm (for example, an elastic image fusion algorithm as described below in the chapter "Definitions"). In particular, the transformations therefore are coordinate transformations and/or mappings between coordinate systems, for example between the coordinate system used to define information contained in the first data set and the coordinate to be used to define information contained in the second data set. In the step of determining the first matching transformation, the first data set is embodied by the image information of the first modality image data and the second data set is embodied by the second modality atlas image. In particular, the first matching transformation and the second modality image representation are determined based on the imaging modality data in order to input information into the disclosed method which imaging modalities are to be considered during execution of the disclosed method.

In particular, the first matching transformation is constituted to match the representation of the anatomical structure in the first modality medical image with the representation of the general structure of the anatomical structure in the first modality atlas image. In the context of this disclosure, a matching transformation contains at least one of a mapping and a matching function. Matching is understood to encompass in particular a spatial adaptation of (in particular positional) information contained in a first data set to (in particular positional) information contained in a second data set. This can happen for example by adaptation of the geometric properties (for example, at least one of size—in particular volume—and shape) of a structure described by both data sets. For example, the representation of the general structure in the first modality atlas image is adapted to the spatial properties of the representation of the anatomical structure in the first modality medical image. In particular, the representation (in particular the geometric properties) of the general representation of the anatomical structure in the first modality atlas image is deformed to fit to the representation in the first modality medical image. The first matching transformation therefore is in particular an elastic transformation which can be implemented as an elastic fusion algorithm. An elastic transformation in the meaning of this disclosure is in particular a transformation which maps a first set of spatial information onto a second set of spatial information while adapting at least the second set to the first set in order to achieve congruence between the two sets of spatial information. In the ideal case, the matching transformation is in the end determined to be unity (or at least optimized to be a value close as close to unity as possible considering in particular a predetermined maximum difference between the matching transformation and unity). In the present case this implies that the representation of the anatomical structure in the first modality atlas image is deformed to constitute a best fit (for example in the sense of a least-squares fitting) to the geometry of the representation of the anatomical structure in the first modality medical image.

Based on the aforementioned information about corresponding anatomical structures in the first modality atlas image and the second modality atlas image, a second modality image representation of the first modality medical image is then preferably determined based on the first matching transformation and the first modality atlas image and the information about the representation of the general structure of the anatomical structure in the second imaging modality (in particular based on the second modality atlas image). The second modality image representation describes what the first modality atlas image (in particular the matched first modality atlas image) would look like if the (matched) general structure had been generated on the basis of medical image data which had been acquired with the second imaging modality. The second modality image representation is preferably determined by replacing the element representation information of the image elements in the (matched) first modality atlas image with the corresponding element representation information for the second imaging modality.

Alternatively and according to a less preferred embodiment, the second modality image representation is determined by determining a modality transformation between the first modality atlas image and the second modality atlas image which again is preferably an elastic fusion transformation for matching the second modality atlas image to the first modality atlas image. In particular, the modality transformation is a transformation between the first modality atlas image which has been matched to the first modality image data (the matched first modality atlas image), and the second modality atlas image. For example, the first matching transformation is applied to the first modality atlas image in order to determine a matched first modality atlas image containing a representation of the general structure of the anatomical structure which has been matched to the representation of the anatomical structure in the first modality medical image. The modality transformation then is preferably determined as a transformation between the matched first modality atlas image and the second modality atlas image. Advantageously, the representation of the anatomical structure in the second modality atlas image is matched (i.e. mapped and deformed) to fit the representation of the anatomical structure in the matched first modality atlas image.

Preferably, a second matching transformation is determined between the second modality image representation and the second modality medical image. The second matching transformation is determined in particular based on the second modality image representation and the second modality image data. Further particularly, the second modality image representation of the anatomical structure is matched (i.e. at least one of mapped and deformed) to fit the representation of the anatomical structure in the second modality medical image. This serves in particular to compare the representation of the anatomical structure in the second modality image representation and in the second modality medical image. In particular, at least one of the spatial properties (for example the positions) and the geometric properties (in particular the shape) of the two representations can be compared and differences can be determined in particular by determining parameters of the second matching transformation which are nonzero. An advantage of conducting the comparison based on the aforementioned method steps is that data processing instabilities which would occur when comparing image representations of different modality can be avoided since the second modality image representation and the second modality medical image contain image information in particular about the anatomical structure which is defined in the same space of colour value, colour contrasts and types of anatomical structures and which therefore in particular use the same set of representation classes (in particular tissue classes) for describing the image information.

The disclosed method can be carried out irrespective of the number of space dimensions to be considered, for example it can be executed in both a two-dimensional and a three-dimensional environment. In particular, any positions and image information (in both the medical images and the atlas images) can be defined in two or three dimensions.

A specific preferred embodiment of the invention is directed to avoiding data processing instabilities in case at least one of a spatial (in particular a positional) and a geometric change (in particular a change in shape) has occurred to the anatomical structure between the point in time at which the first modality image data was generated and the point in time at which the second modality image data was generated. For example, the second modality medical image may display a comparably large positional shift of the outer brain surface compared to the position of the outer brain surface in the first modality medical image and therefore in the second modality image representation. This positional shift may be due to for example a loss of surface tension on the outer surface of the brain below the position of a craniotomy which may lead to a collapse of the brain structure in the gravitation of field, in particular away from the position of the craniotomy. This positional shift may, however, lead to data processing instabilities when matching the second modality medical image to the second modality image representation. In particular, a large positional shift may hamper automatic detection of anatomical structures corresponding to each other in both representations. In order to avoid this problem, the present invention preferably comprises a step of defining a structural change region in the second modality image representation. The structural change of the region comprises in particular a placeholder for a data structure which represents a change of the anatomical structure. The placeholder is in particular a seed structure which can be used in particular for adapting the second matching transformation to the change of the anatomical structure, in particular to a difference to the representations of the anatomical structure in the second modality representation and the second modality medical image. For example, the placeholder can be expanded in the second modality image representation by applying a field of shift vectors to the placeholder and correspondingly shifting and/or deforming the structures in the second modality image representation which surround the placeholder. The expansion is preferably carried out until the placeholder corresponds to the difference in representation to a predetermined degree of similarity.

Preferably, similarity data describing a measure of similarity between the second modality image representation and the second modality medical image (in particular between the respective representations of the anatomical structure) is determined. The measure of similarity is determined based on for example a similarity between the second modality image representation and the second modality image based on comparing the representation classes of the respective image elements describing the anatomical structure in the second modality image representation and the second modality medical image, respectively. The measure of similarity preferably includes (in particular is) a cross-correlation, for example a local-cross-correlation between colour contrasts in the second modality image representation and colour contrast in the second modality medical image. Alternatively or additionally, it includes (in particular is) a local cross-correlation between colour values in the second modality image representation and colour values in the second modality medical image. As a preferred embodiment, regions in the second modality image representation and the second modality medical image for which at least substantially no similarity (in particular no similarity and/or a low value of the measure of similarity) has been determined are excluded as a basis for determining the second matching transformation. This avoids hampered data processing when determining the second matching transformation. Alternatively or additionally, a structural change region may be defined in a region of at least substantially no similarity and the placeholder may be expanded. The similarity data may then be re-determined in particular until a predetermined value (in particular an acceptable level) of the measure of similarity is determined. Thereby, information about a structural change of the anatomical structure and a change of at least one of shape, size and position of the constituents of the anatomical structure which had already been represented in the first modality medical image can be determined in a concise manner.

The structural change region may alternatively or additionally be also in particular an anatomical feature which is represented in the first modality medical image and therefore the second modality image representation, but is not represented in the second modality medical image (for example, an implant or a tumour which has been implanted or grown, respectively, in the meantime). In this case, the change region is preferably defined in the second modality image representation at the position of the respective anatomical structure, which is then compressed for example by applying a vector field in an inward direction of an anatomical structure in order to reduce it and it is no longer present and a predetermined level of similarity to the second modality medical image is reached.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

DEFINITIONS

In this chapter, definitions are disclosed which define terminology used in the present disclosure. These definitions also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer, a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. The MRI scans represent an example of an imaging method.

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps and acquiring steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "subcomputers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined in particular by the information which they describe which is preferably called "XY information".

The first and second matching transformations are for example image fusion transformations, in particular elastic fusion transformations which are designed to enable a seamless transition from one data set (e.g. first data set, e.g. first image) to another data set (e.g. second data set, e.g. second image). In this application, the term "image morphing" is also used as an alternative to the term "image fusion", but with the same meaning. The transformations are is in particular designed such that one of the aforementioned first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are in particular vectors of a deformation field F. These vectors are determined by the optimization algorithm which results in an optimum degree of similarity. Thus, the optimum degree of similarity represents a condition, in particular a constraint, for the optimization algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimizing problem is in particular solved iteratively, in particular by means of an optimization algorithm which is in particular a first-order optimization algorithm, in particular a gradient descent algorithm. Other examples of optimization algorithms include optimization algorithms which do not use derivations such as the downhill simplex algorithm or algorithms which use higher-order derivatives such as Newton-like algorithms. The optimization algorithm preferably performs a local optimization. If there are a plurality of local optima, global algorithms such as simulated annealing or genetic algorithms can be used. In the case of linear optimization problems, the simplex method can for instance be used.

In the steps of the optimization algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighboring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

DESCRIPTION OF THE FIGURES

In the following, a preferred embodiment of the present invention is described with reference to the figures, without limiting the present invention to the features which are described in the following and shown in the figures, wherein FIG. 1 describes a general algorithm used for determining the second modality image representation.

Figure 1:
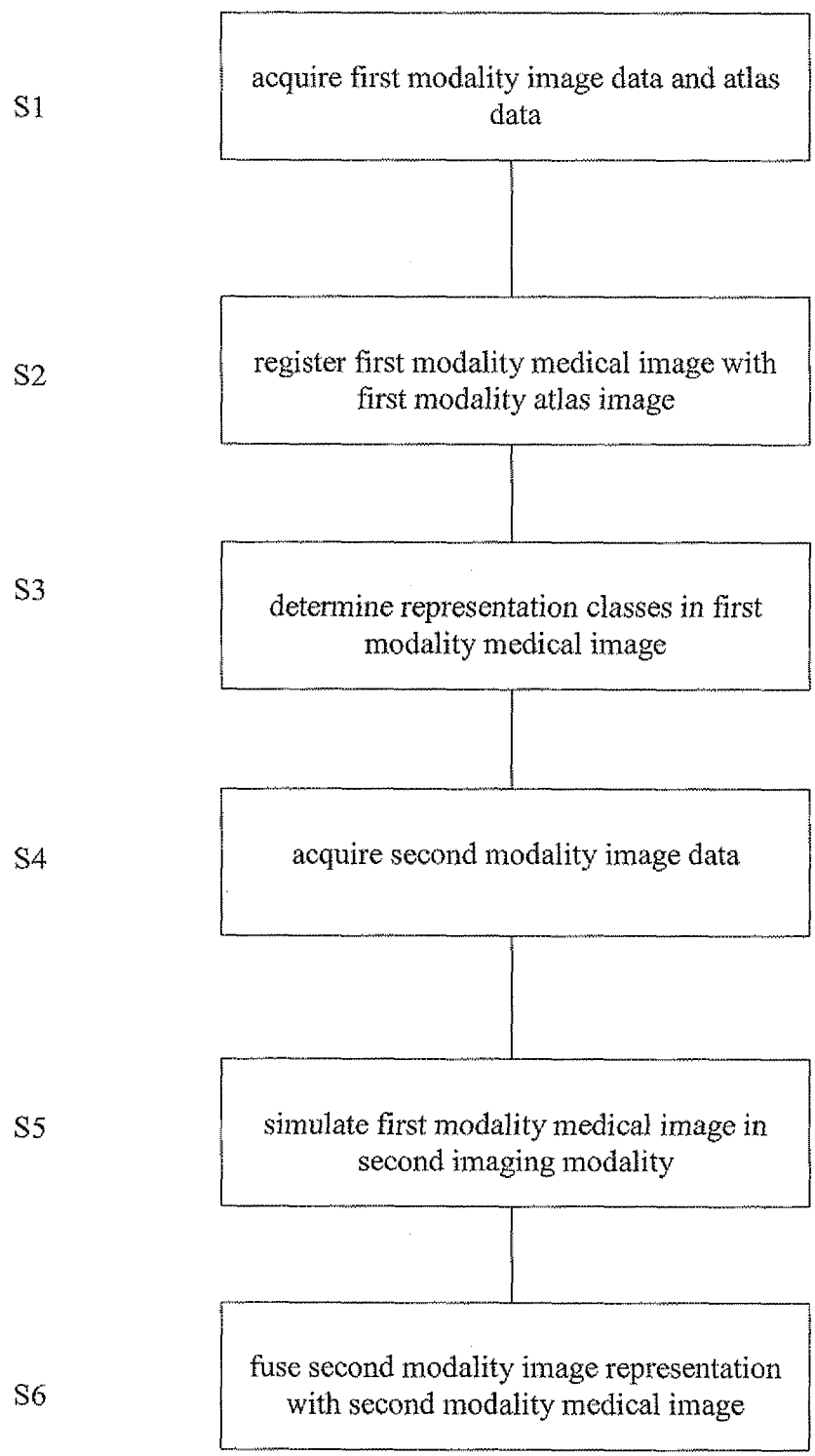

According to FIG. 1, the first modality image data and the atlas data is acquired in step S1. The first modality medical image is then registered with the first modality atlas image in step S2 in particular by determining the first matching transformation. Then, the method carries on in steps S3 with segmenting the representation classes in the first modality medical image for example by applying an expectation maximization algorithm. In step S4, the second modality image data is acquired. Preferably, the first modality image data comprises imaging modality data describing the type of imaging modality which is the first imaging modality. Preferably, the second modality image data comprises imaging modality data which describes the type of imaging modality which is the second imaging modality.

In step S5, the first modality medical image is then simulated in the second imaging modality by determining the second modality image representation. This simulation is carried out in particular based on the results of the segmentation in step S3 an information contained in the atlas data which describes how a given representation class (in particular tissue type) appears in the first imaging modality and in the second imaging modality.

In order to compare the representation of the anatomical structure in the first modality medical image (in particular in the second modality image representation) with its representation in the second modality medical image, an elastic fusion is performed in step S5 between the second modality image representation and the second modality medical image. This elastic fusion is an example of the second matching transformation.

A specific example of the workflow shown in FIG. 1 is the following: a patient usually undergoes several pre-operative MR scans, for example a $T_1$ and a $T_2$ scan. Different types of tissue can be determined from the images taken in $T_1$ and $T_2$, respectively, and a combined data set representing the first modality image data can be generated from the $T_1$ and $T_2$ images. The first imaging modality therefore is set to be MR. Later on, a CT image may be taken of the patient, and the second imaging modality therefore is CT. Based on an information about the Hounsfield values for specific types of tissue in the CT image, a CT is simulated from the combined $T_1$ and $T_2$ data set (i.e. from the first modality image data. This results in one genuine and one simulated CT data set, and these two data sets can be fused with a higher stability than would be the case when using a multi-modal MR-CT fusion algorithm which uses for example mutual information.

Figure 2:
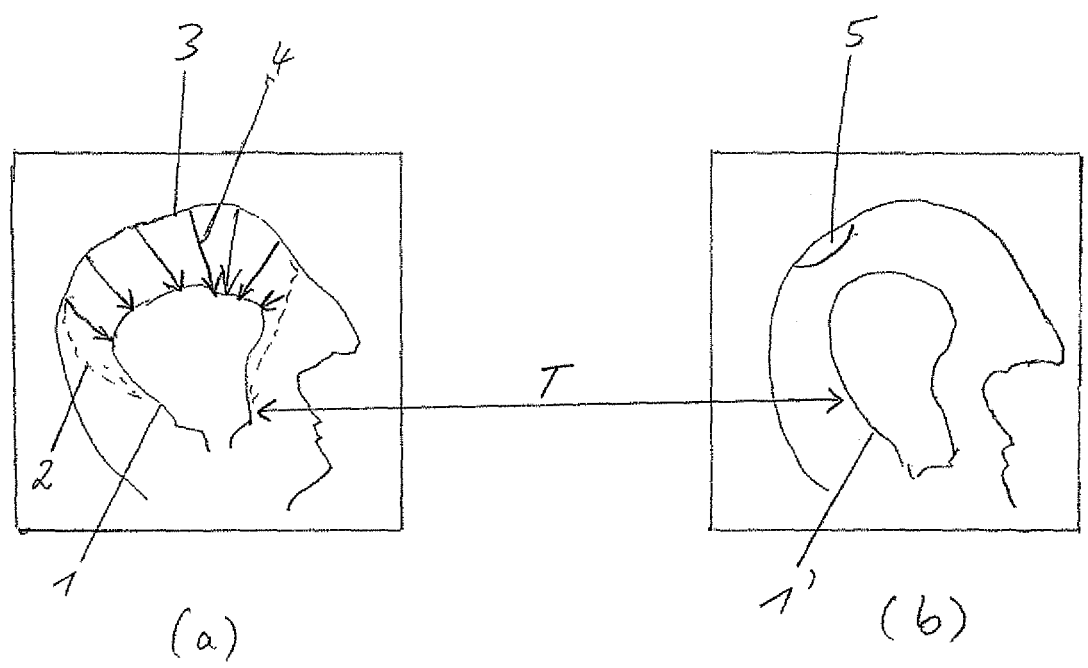
FIG. 2 illustrates the meaning of a structural change region.

FIG. 2 shows how a structural change region is used to support determining the second matching transformation. FIG. 2(a) illustrates a second modality image representation of an anatomical structure embodied by a patient's brain 1 which, before growing a placeholder 3, extends along its outer boundary 2 almost up to the inner surface of the skull bones. Preferably, a structural change region is defined comprising the placeholder 3. FIG. 2(b) illustrates a second modality medical image of the same patient's skull and brain 1' along with a craniotomy 5, due to which the brain 1' collapsed compared to its outer boundary 2 shown in FIG. 2(a). In order to support determining the second matching transformation T for an anatomical structure represented by the brain between the images of FIGS. 2(a) and (b), a placeholder 3 is inserted for example along the original boundary 2 of the brain 1 in the second modality image representation. The placeholder 3 is then grown by applying a vector field or to the image elements representing the placeholder 3. Thereby, a cavity is grown in the second modality image representation so that the difference in appearance of the brain 1, 1' between the two images becomes similar. Thereby, it is avoided that the cavity which was generated by the brain collapsing and is depicted in the second modality medical image leads to a fault in determining the second matching transformation T since no corresponding cavity would have been found in the second modality image representation before growing the placeholder.

The invention claimed is:
1. A system, comprising:
at least one medical imaging device for generating patient images of a patient; and
at least one computer for transforming a representation of an anatomical structure of a patient in a first imaging modality into a representation of the anatomical structure in a second, other imaging modality, the computer having memory and instructions that when executed, perform the following steps:
acquire first modality image data describing a first modality medical image generated by the medical imaging device, the first modality medical image containing the representation of the anatomical structure in the first imaging modality;
acquire atlas data describing a first modality atlas image describing a general structure of the anatomical structure in the first imaging modality, the atlas data containing information about the representation of the general structure in the second imaging modality;
determine, used on the first modality image data and the atlas data, a first matching transformation between the first modality medical image and the first modality atlas image;
determine, based on the first matching transformation and the first modality atlas image and the information about the representation of the general structure in the second imaging modality, a second modality image representation of the first modality medical image;

acquire second modality image data describing a second modality medical image containing the representation of the anatomical structure in the second imaging modality;

determine based on the second modality image representation and the second modality image data, a second matching transformation between the second modality image representation and the second modality medical image;

define a structural change region in the second modality image representation, the structural change region including a placeholder representing a structural change of the anatomical structure; and adapt the second matching transformation to a difference between the representations of the anatomical structure in the second modality representation and the second modality medical image by modifying the placeholder.

2. A computer implemented method of transforming a representation of an anatomical structure of a patient in a first imaging modality into a representation of the anatomical structure in a second, other imaging modality, comprising:

acquiring, at one or more processors of the computer, first modality image data describing the first modality medical image containing the representation of the anatomical structure in the first imaging modality;

acquiring, at one or more of the processors of the computer, atlas data describing a first modality atlas image describing a general structure of the anatomical structure in the first imaging modality, the atlas data containing information about the representation of the general structure in the second imaging modality;

determining, by one or more of the processors of the computer and based on the first modality image data and the atlas data, a first matching transformation between the first modality medical image and the first modality atlas image;

determining, by one or more of the processors of the computer and based on the first matching transformation and the first modality atlas image and the information about the representation of the general structure in the second imaging modality, a second modality image representation of the first modality medical image;

acquiring, at one or more of the processors of the computer, second modality image data describing a second modality medical image containing the representation of the anatomical structure in the second imaging modality;

determining, by one or more of the processors of the computer and based on the second modality image representation and the second modality image data, a second matching transformation between the second modality image representation and the second modality medical image;

defining, by one or more of the processors of the computer, a structural change region in the second modality image representation, the structural change region comprising a placeholder for a data structure representing a structural change of the anatomical structure; and adapting the second matching transformation to a difference between the representations of the anatomical structure in the second modality representation and the second modality medical image by modifying the placeholder.

3. The method according to claim 2, wherein a matched first modality atlas image is determined by applying the first matching transformation to the first modality atlas image, and wherein the first matching transformation is determined based on the matched first modality atlas image.

4. The method according to claim 2, wherein the atlas data describes a second modality atlas image describing a general structure of the anatomical structure in the second image modality, and wherein the information about the representation of the general structure in the second imaging modality is determined based on the second modality atlas image.

5. The method according to claim 4, wherein the second modality image representation is determined based on determining a modality transformation between the matched first modality atlas image and the second modality atlas image.

6. The method according to claim 5, comprising:

acquiring, at one or more of the processors of the computer, representation class data describing a representation class of the image elements describing the representation of the general structure of the anatomical structure in the first imaging modality and in the second imaging modality, wherein the representation class describes at least one of colour contrasts, colour values and type of physical structure represented by the image elements, wherein the modality transformation is determined based on the representation class data.

7. The method according to claim 2, comprising:

acquiring, at one or more of the processors of the computer, imaging modality data describing the first imaging modality and the second imaging modality, wherein the first matching transformation and the second modality image representation are determined based on the imaging modality data.

8. The method according to claim 7, wherein also the second matching transformation is determined based on the imaging modality data.

9. The method according to claim 7, wherein the representation class describes a grey value.

10. The method according to claim 7, comprising:

determining, by one or more of the processors of the computer, similarity data describing a measure of similarity between the second modality image representation and the second modality medical image, wherein the measure of similarity is determined based on a similarity between the second modality image representation and the second modality medical image with regard to the representation class of the respective image elements describing the anatomical structure.

11. The method according to claim 10, wherein the measure of similarity includes a cross-correlation between at least one of colour contrasts and colour values in the second modality image representation and the second modality medical image.

12. The method according to claim 9, wherein regions in the second modality image representation and the second modality medical image for which at least substantially no similarity has been determined are excluded as a basis for determining the second matching transformation.

13. The method according to claim 2, wherein the first matching transformation and the second matching transformation are determined based on executing at least one of an image segmentation algorithm and an image fusion algorithm.

14. The method according to claim 2, wherein the first imaging modality is magnetic resonance tomography and the second medical imaging modality is computed x-ray tomography or x-ray.

15. A non-transitory computer-readable storage medium embodying a computer program which, when running on a computer or when loaded onto a computer, causes the computer to perform a method of transforming a representation of an anatomical structure of a patient in a first imaging modality into a representation of the anatomical structure in a second, other imaging modality, the method comprising the following steps:

acquiring first modality image data describing the first modality medical image containing the representation of the anatomical structure in the first imaging modality;

acquiring atlas data describing a first modality atlas image describing a general structure of the anatomical structure in the first imaging modality, the atlas data containing information about the representation of the general structure in the second imaging modality;

determining, based on the first modality image data and the atlas data, a first matching transformation between the first modality medical image and the first modality atlas image;

determining, based on the first matching transformation and the first modality atlas image and the information about the representation of the general structure in the second imaging modality, a second modality image representation of the first modality medical image;

acquiring second modality image data describing a second modality medical image containing the representation of the anatomical structure in the second imaging modality;

determining based on the second modality image representation and the second modality image data, a second matching transformation between the second modality image representation and the second modality medical image;

defining a structural change region in the second modality image representation, the structural change region comprising a placeholder for a data structure representing a structural change of the anatomical structure; and adapting the second matching transformation to a difference between the representations of the anatomical structure in the second modality representation and the second modality medical image by modifying the placeholder.

16. A computer having a digital processor and a memory, wherein the computer program according to claim 15 is running on the processor or is loaded into the memory.

* * * * *